(12) United States Patent
Nestenborg et al.

(10) Patent No.: US 7,066,912 B2
(45) Date of Patent: Jun. 27, 2006

(54) CATHETER WETTING APPARATUS

(75) Inventors: Daniel Nestenborg, Branno (SE); Jan Utas, Kungsbacka (SE); Agneta Pettersson, Molndal (SE)

(73) Assignee: Astra Tech AB, Molndal (SE)

(*) Notice: Subject to any disclaimer, the term of this patent is extended or adjusted under 35 U.S.C. 154(b) by 387 days.

(21) Appl. No.: 10/168,091

(22) PCT Filed: Dec. 18, 2000

(86) PCT No.: PCT/SE00/02566

§ 371 (c)(1),
(2), (4) Date: Sep. 17, 2002

(87) PCT Pub. No.: WO01/43807

PCT Pub. Date: Jun. 21, 2001

(65) Prior Publication Data

US 2003/0055403 A1    Mar. 20, 2003

(30) Foreign Application Priority Data

Dec. 17, 1999  (SE) .................................... 9904635

(51) Int. Cl.
 A61M 5/00     (2006.01)
 A61M 5/32     (2006.01)
 A61M 27/00    (2006.01)
 A61F 5/44     (2006.01)

(52) U.S. Cl. ............... 604/171; 604/172; 604/265; 604/544; 604/328; 206/364; 206/571

(58) Field of Classification Search ........... 604/171, 604/172, 265, 266, 267, 540, 544, 327, 328; 206/363, 438, 571, 364, 365, 366, 210
See application file for complete search history.

(56) References Cited

U.S. PATENT DOCUMENTS

| | | | | |
|---|---|---|---|---|
| 1,120,549 A | * | 12/1914 | Schelberg ................. 604/171 |
| 2,856,932 A | * | 10/1958 | Griffitts .................... 604/171 |
| 3,035,691 A | * | 5/1962 | Rasmussen et al. ...... 206/364 |
| 3,345,988 A | * | 10/1967 | Vitello ..................... 604/172 |
| 3,648,704 A | * | 3/1972 | Jackson ................... 604/172 |
| 3,861,395 A | * | 1/1975 | Taniguchi ................. 604/172 |
| 3,898,993 A | * | 8/1975 | Taniguchi ................. 604/172 |
| 3,926,309 A | * | 12/1975 | Center ..................... 206/364 |
| 3,934,721 A | * | 1/1976 | Juster et al. .............. 206/364 |
| 3,967,728 A | * | 7/1976 | Gordon et al. ............ 206/364 |
| 4,091,922 A | * | 5/1978 | Egler ....................... 206/364 |
| 4,230,115 A | * | 10/1980 | Walz et al. ............... 604/517 |
| 4,269,310 A | * | 5/1981 | Uson ....................... 206/210 |
| 4,366,901 A | * | 1/1983 | Short ....................... 206/210 |

(Continued)

FOREIGN PATENT DOCUMENTS

WO    97/26937    7/1997

(Continued)

*Primary Examiner*—Tatyana Zalukaeva
*Assistant Examiner*—Michael G Bogart
(74) *Attorney, Agent, or Firm*—Birch Stewart Kolasch & Birch LLP

(57) ABSTRACT

A wetting apparatus (1) for wetting a hydrophilic urinary catheter (3), comprising: a wetting fluid container (4) containing a wetting fluid and being openable by the application of a pulling force thereto; a wetting receptacle (2); and a hydrophilic urinary catheter (3) to be wetted by said wetting fluid and being arranged within said wetting receptacle (2). The wetting fluid container (4) is arranged within the wetting receptacle (2), and the wetting receptacle is extendable, for opening the wetting container without rupturing a sealed condition of the wetting receptacle.

30 Claims, 4 Drawing Sheets

U.S. PATENT DOCUMENTS

| | | | | |
|---|---|---|---|---|
| 4,379,506 | A | * | 4/1983 | Davidson .................... 206/364 |
| 4,597,765 | A | * | 7/1986 | Klatt ....................... 623/23.67 |
| 4,692,154 | A | * | 9/1987 | Singery et al. ............. 604/172 |
| 4,754,877 | A | * | 7/1988 | Johansson et al. .......... 206/364 |
| 4,772,275 | A | * | 9/1988 | Erlich ........................ 604/523 |
| 4,811,847 | A | * | 3/1989 | Reif et al. .................. 206/571 |
| 5,105,942 | A | * | 4/1992 | van Veen et al. ........... 206/364 |
| 5,125,416 | A | * | 6/1992 | Phillips ...................... 600/585 |
| 5,147,341 | A | * | 9/1992 | Starke et al. ............... 604/349 |
| 5,226,530 | A | * | 7/1993 | Golden ....................... 206/210 |
| 5,454,798 | A | * | 10/1995 | Kubalak et al. ............. 604/328 |
| 5,738,213 | A | * | 4/1998 | Whiting et al. ............. 206/364 |
| 5,853,518 | A | * | 12/1998 | Utas ........................... 156/245 |
| 6,065,597 | A | * | 5/2000 | Pettersson et al. .......... 206/364 |
| 6,409,717 | B1 | * | 6/2002 | Israelsson et al. .......... 604/544 |
| 6,736,805 | B1 | * | 5/2004 | Israelsson et al. .......... 604/544 |
| 6,848,574 | B1 | * | 2/2005 | Israelsson et al. .......... 206/210 |

FOREIGN PATENT DOCUMENTS

WO          98/11932          3/1998

* cited by examiner

CATHETER WETTING APPARATUS

This application is the national phase under 35 U.S.C. § 371 of PCT International Application No. PCT/SE00/02566 which has an International filing date of Dec. 18, 2000, which designated the United States of America.

FIELD OF THE INVENTION

The present invention relates to a wetting apparatus for wetting a hydrophilic urinary catheter, comprising a wetting fluid container containing a wetting fluid and being openable by the application of a pulling force thereto, a wetting receptacle and a hydrophilic urinary catheter to be wetted by said wetting fluid and being arranged within said wetting receptacle. The invention further relates to a method for wetting such a catheter.

BACKGROUND OF THE INVENTION

Intermittent self-catheterisation is widely employed by patients suffering from for example strictures or traumas in the urinary system as well as by paralysed patients to enable the patients to live a nearly normal home life. Urinary catheters supplied for intermittent self-catheterisation in general need to have a lubricant applied to the outer surfaces thereof to facilitate insertion into the urethra. Especially, for lubrication purposes hydrophilic urinary catheters may have a hydrophilic outer surface coating which should be wetted by a fluid such as water or saline for a certain time period prior to insertion thereof into the urethra of a patient.

Various methods for lubricating urinary catheters have been previously proposed, and e.g. the applicant's prior International patent application publication No. WO97/26937 discloses a wetting apparatus for wetting hydrophilic urinary catheters. This wetting apparatus comprises a wetting receptacle, which defines a wetting fluid receiving area, a hydrophilic urinary catheter placed in said wetting fluid receiving area, and a wetting fluid container. The wetting fluid container has a discharge outlet which could be opened by application of a pulling force thereto to enable the wetting fluid to be discharged into the wetting fluid receiving area for wetting of the hydrophilic urinary catheter. In this wetting apparatus the receptacle has one open end, in which the fluid container is placed, and with one end protruding out of the receptacle. Further, pulling tabs to apply the pulling force to the container are arranged at each end of the fluid container. To release the fluid, the first pulling tab being inside the receptacle is gripped through the plastic material of the receptacle, and then the second pulling tab being outside the receptacle is pulled rearwardly to cause the container to tear.

Further, a urinary catheter wetting apparatus comprising a receptacle and a rupturable liquid swelling medium pouch or container being placed within the receptacle is known from WO 98/11932. The swelling medium is discharged by applying pressure on the pouch and thereby forcing a rupture on the closure joint.

However, a problem with these known wetting apparatuses is that they are relatively difficult to handle, and especially the discharging of the wetting fluid. Particularly disabled users, such as users with limited capability of moving their limbs, have problems performing the discharging actions needed. Furthermore, it is a problem that the wetting receptacle surrounding the catheter is either opened during the discharge process, or is easily ruptured. This deteriorates the cleanness and sterility of the catheter. There is hereby also a risk for unwanted leakage and spillage of the wetting fluid, which could be very inconvenient for the user.

Accordingly, patients using hydrophilic urinary catheters require improved means for lubricating the catheters. The present invention therefore proposes to address this requirement. This object is achieved with the wetting apparatus and method according to the appended claims.

SUMMARY OF THE INVENTION

According to a first aspect of the invention there is provided a wetting apparatus for wetting a hydrophilic urinary catheter, comprising: a wetting fluid container containing a wetting fluid and being openable by the application of a pulling force thereto; a wetting receptacle; and a hydrophilic urinary catheter to be wetted by said wetting fluid and being arranged within said wetting receptacle, wherein the wetting fluid container is arranged within and fixed to the wetting receptacle, said apparatus being characterised in that the wetting receptacle is extendable, enabling opening the wetting container without rupturing a sealed condition of the wetting receptacle.

Thus, according to the invention the wetting fluid container can be opened and the catheter wetted by the application of a pulling force to the extendable wetting receptacle, without destroying the sealed condition of the wetting receptacle.

By "extendable" is meant that the dimension of the wetting receptacle in a certain pulling direction could be increased without causing damages or destruction to the receptacle to such an extent that the sealed condition of the receptacle is destroyed.

The pulling action for discharging the wetting fluid into the wetting receptacle is a very feasible action, since it is easy to perform and only requires a low pulling force to be exerted. Further, the pulling action could be performed with one hand only, or even without hands, by using the teeth or the like. Thus, this discharging method is suitable for disabled persons, or persons having one or both hands occupied. Thanks to the extendable wetting receptacle this preferred pulling action could be used for discharging the wetting fluid, at the same time as the wetting receptacle could be kept closed and sealed. Hereby, the sterility and cleanness of the catheter could be maintained even during the wetting process, thus reducing the risk of infections for the user. The risk of unwanted leakage and spillage of the wetting liquid is also alleviated.

Preferably, the wetting fluid container is provided with at least two pulling means for applying a pulling force for opening the container.

By "pulling means" is meant any means providing a transfer of a pulling force applied to the wetting receptacle to the wetting fluid container, such as a portion of the container being fixed to the receptacle.

Further, the wetting fluid container is preferably opened by pulling said pulling means apart in a separation direction, said wetting receptacle being extendable at least in said separation direction. It is also preferred that at least one of the pulling means, and preferably both, is a tab which on application of a predetermined pulling force thereto causes the wetting fluid container to open. These features contribute in making the product simple and inexpensive to manufacture.

In a preferred embodiment of the invention the wetting fluid container presents at least one surface area not being fixed to the wetting receptacle and, most preferably, the wetting fluid container is fixed to the wetting receptacle only in the vicinity of the pulling means. Hereby, as large a part of the wetting receptacle as possible could be used for providing the extendability. Further, the pulling means are preferably fixed to the wetting receptacle by means of welding. However, glue or tape could be used as fixation means as well. Hereby, the manufacture of the product becomes simple and inexpensive.

In one embodiment there is further provided pulling means on the wetting receptacle, such as pulling handles, to facilitate the opening procedure, especially for disabled users.

According to one embodiment of the invention, the wetting receptacle is at least partly formed of a stretchable material, enabling the extendability of the receptacle. Said stretchable material could be at least partly elastic. However, a material enabling a plastic elongation of the receptacle could also be used.

According to another, preferred embodiment of the invention, the wetting receptacle has a surface layer of such dimension as to enable the extendibility of the receptacle. Preferably the surface layer of the wetting receptacle has a dimension between the pulling means exceeding the distance between the pulling means, when the wetting fluid container is not opened, and most preferably the wetting receptacle comprises a folded section, such as a bellow-like folding.

Preferably, the wetting fluid container presents such a restricted dimension perpendicular to the pulling direction in which said folded section is unfolded, that said unfolding is not restricted by the wetting fluid container. Especially, it is preferred that the wetting receptacle, at said folded section has an inner, cross-sectional dimension perpendicular to the direction of the extension of the receptacle significantly exceeding the corresponding outer, cross-sectional dimension of the wetting fluid container. Thanks to this increased extension, unfoldment of the folded section becomes simple.

It is also preferred that the wetting fluid container comprises an area of weakness, and preferably a tear line, which is opened on the application of the pulling force thereto.

In a preferred embodiment of the invention said area of weakness in the wetting fluid container is arranged in a part of the container facing the catheter in the wetting receptacle. Further, it is most preferred that the wetting fluid container presents a forward edge facing the catheter in the wetting receptacle; that the area of weakness extends rearwardly from the forward edge; and that the wetting container comprises two tabs of which a first tab extends rearwardly from the forward edge on a first side of the area of weakness and is of such dimensions that it rearwardly projects beyond the wetting fluid container, and of which a second tab extends forwardly from the forward edge on a second, opposite side of the area of weakness; wherein the application of a rearward pulling force on the first tab relative to the second tab causes the area of weakness to tear and the wetting fluid container to be opened.

This embodiment provides an area of weakness essentially aligned with the catheter and thus with the elongation of the wetting apparatus, and the pulling direction also coincide with this direction. Hereby, the discharging action becomes simple since essentially the whole extent of the wetting receptacle may be used as a grip.

In an alternative embodiment, the wetting fluid container presents a forward edge facing the catheter in the wetting receptacle; the area of weakness extends rearwardly from the forward edge; the container comprises two tabs, of which a first tab extends laterally relative to the forward edge on a first side relative to the area of weakness, and of which a second tab extends laterally from the forward edge on a second, opposite side of the area of weakness relative to the first tab; wherein the application of a predetermined lateral pulling force on the first tab relative to the second tab causes the area of weakness to tear and the wetting fluid container to be opened.

The wetting apparatus according to this embodiment is easy to manufacture, especially since the wetting fluid container may be fixed directly to the sides of the receptacle, whereby no additional and more complicated pulling means are needed.

In still another embodiment, the area of weakness in the wetting fluid container is extending in an oblique angle to a direction towards the catheter in the wetting receptacle. Preferably, the area of weakness extends in about 45° angle relative to the direction towards the catheter, but it may also be another angle, such as essentially perpendicular to this direction. It is in this embodiment preferred that the wetting fluid container presents a forward edge facing the catheter in the wetting receptacle and a rearward edge facing away from the catheter in the wetting receptacle, whereby the area of weakness extends between the forward and rearward edge; the container comprises two tabs, of which a first tab extends forwardly on the forward edge on the side closest to the area of weakness, and of which a second tab extends rearwardly from the rearward edge on the side closest to the area of weakness; and application of a predetermined rearward pulling force on the first tab relative to the second tab causes the area of weakness to tear and the wetting fluid container to be opened.

The wetting apparatus according to this embodiment is also easy to manufacture, since the wetting fluid container may be fixed directly to the sides of the receptacle, whereby no additional and more complicated pulling means are needed. At the same time, a pulling direction essentially aligned with the extension of the wetting apparatus may be used, which facilitates the opening process, especially for disabled persons.

In preferred embodiments of the invention the fluid container takes the form of a sachet.

It is further preferred that the wetting fluid is sterile water or a saline solution.

A typical sterilising agent which could be used for sterilising the wetting apparatus of the invention is ethylene oxide. Moreover, the fluid in the fluid container would normally be sterile. For these reasons, the wetting fluid container is preferably made of a material which is impermeable or substantially impermeable to ethylene oxide as well as the fluid contained therein. Non-limiting examples of materials satisfying this condition when the fluid is water or saline are aluminium foil laminate, poly(vinylidene chloride) or a laminate comprising metallised film such as metallised poly(ethylene terepthalate), or a silicon oxide coated film.

The wetting receptacle according to the invention may be used only for keeping the catheter clean and sterile and for the described wetting process, and is thereafter disposed. However, in one embodiment the wetting receptacle is also a urine collection bag.

The present invention has the advantage of providing a safe, compact, sterile and disposable wetting apparatus for a hydrophilic urinary catheter, which is easy to handle. This is due to the provision of a wetting receptacle which is adapted to cooperate with a wetting fluid container of the apparatus so as to be able to release the fluid into the wetting receptacle to wet a hydrophilic urinary catheter placed therein under clean conditions, that is to say, without the need for touching the catheter or the fluid, or even breaking the receptacle. Hereby, the risk of introducing contaminants is avoided, and a wetting apparatus that is easy to handle as well as to manufacture is provided.

According to another, second aspect of the invention there is provided a wetting receptacle containing: a wetting fluid container containing a wetting fluid; and a hydrophilic urinary catheter to be wetted by said wetting fluid, both being arranged within said wetting receptacle, wherein the receptacle is movable from an initial closed and non-extended first position to an extended but still closed second position.

According to one embodiment of this second aspect of the invention, the wetting receptacle is at least partly formed of a stretchable material, enabling bringing of the receptacle from the first to the second position.

According to another embodiment of this second aspect of the invention, the receptacle has an inherent elongation, enabling bringing of the receptacle from the first to the second position, and preferably this inherent elongation comprises a bellow-like folding. Hereby, the expandability is achieved without any special requirements on the material, which makes the manufacture simple and inexpensive.

It is further preferred that the receptacle, in the area of said folding, has an inner, cross-sectional extension perpendicular to the direction of said inherent elongation significantly exceeding the corresponding outer, cross-sectional extension of the wetting fluid container.

According to a third aspect of the invention, there is provided a method for wetting a hydrophilic urinary catheter placed in a wetting receptacle together with a wetting fluid container containing a wetting fluid, characterised by the step of applying a pulling force to the wetting receptacle, without opening the latter, for transferring the pulling force via the wetting receptacle to the wetting container to open the latter and discharging the wetting fluid from the thus opened wetting fluid container into the still unopened wetting receptacle.

In an embodiment according to this third aspect of the invention said transfer of the pulling force is accomplished by an elongation of the wetting receptacle. It is further preferred that the transfer of the pulling force is accomplished by the use of at least two pulling means being fixed to the wetting receptacle, whereby the pulling force is applied in such a way that the pulling means are pulled apart.

BRIEF DESCRIPTION OF THE DRAWINGS

By way of example embodiments of the invention will now be described with reference to the accompanying drawings in which.

DESCRIPTION OF PREFERRED EMBODIMENTS

Figure 1:
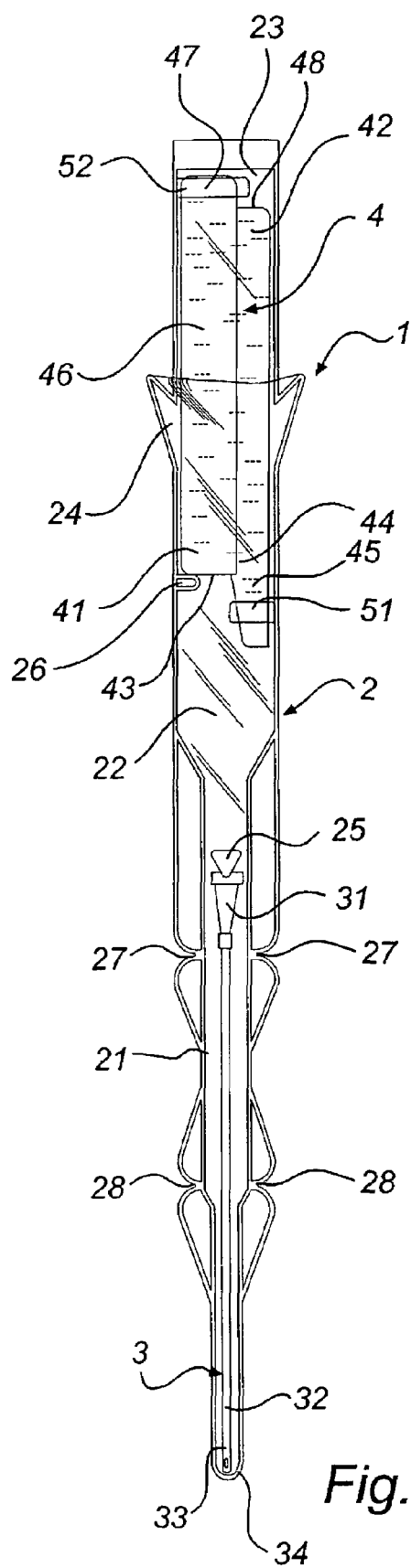
FIG. 1 shows a wetting apparatus according to an embodiment of the invention comprising a wetting receptacle and an unopened wetting fluid sachet.

Referring first to FIG. 1, there is shown a first embodiment of a wetting apparatus 1 according to the invention comprising a wetting receptacle, or bag 2, preferably of a transparent flexible plastics material. The receptacle 2 has a downwardly extending elongate pocket 21 at the forward end, an intermediate chamber 22 rearwardly of and in fluid communication with the elongate pocket 21 and a fluid supply chamber 23 spaced further rearwardly.

The wetting apparatus further comprises a hydrophilic urinary catheter 3 having a flared rearward portion 31, an elongate shaft 32 projecting forwardly from the rearward portion 31 and an open-ended lumen (not shown) which extends from the rear end of the rearward portion 31 to a drainage aperture 33 in the rounded tip 34. The rearward end 31 of the catheter 3 is connectable to a urine collection bag.

Figure 2:
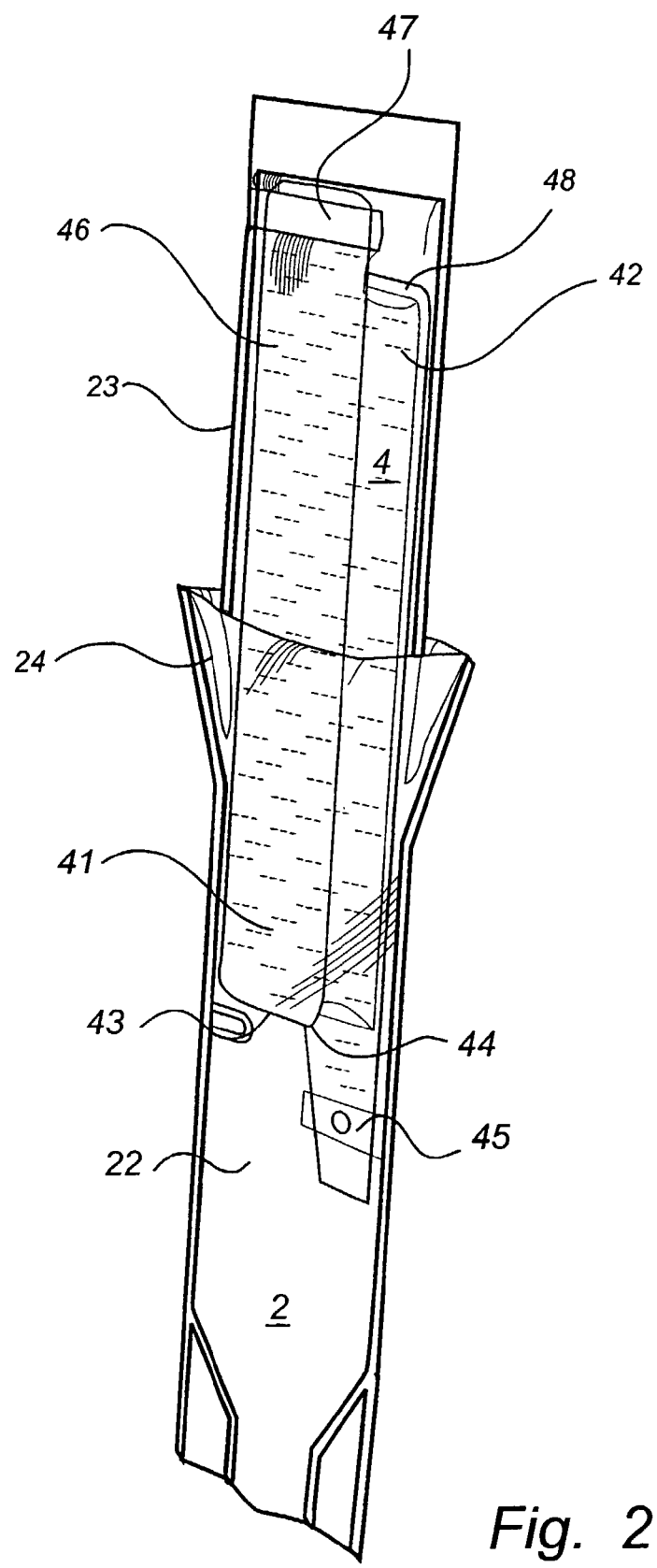
FIG. 2 shows the part of the wetting apparatus shown in FIG. 1 comprising the unopened sachet more in detail.

Further, the wetting apparatus comprises a wetting fluid container 4, which in this embodiment takes the form of a sachet, containing a wetting fluid. As can be seen more particularly by reference to FIG. 2, the sachet 4 is arranged in the fluid supply chamber 23 in an operational position. The sachet 4 has a forward portion 41 which in the operational position of the sachet 4 faces the catheter and the fluid receiving area 21 and a rearward portion 42 which in the operational position projects rearwardly away from the catheter and the fluid receiving area 21. The sachet 4 is preferably made of aluminium foil laminate, poly(vinylidene chloride) or a laminate containing a metallised film, such as metallised poly(ethylene terepthalate), or a silicon oxide coated film, particularly when ethylene oxide is the sterilising agent for the apparatus 1 and the sachet contains sterile water or saline solution.

Preferably, the forward portion 41 of the sachet 4 presents a forward edge 43. Extending rearwardly from the forward edge 43 is an area of weakness, and preferably a tear line 44. Projecting forwardly from the forward edge 43 of the sachet to one side of the tear line 44 is a first tab 45. On the other side of the tear line 44 there is provided an elongate second tab 46, shown here in an extended position in which the second tab 46 projects forwardly from the forward edge 43. The elongate second tab 46 is movable about the forward edge 43 back on it self from the extended position to a retracted position in which the second tab 46 extends rearwardly from the forward edge 43. When the second tab 46 is in the retracted position the sachet 4 is inserted into the fluid supply chamber into the operational position shown in FIG. 1.

Preferably the dimensions of the second tab 46 are such that when the sachet 4 is in the operational position a pulling portion 47 of the second tab 46 projects rearwardly beyond a rearward edge 48 of the sachet 4.

The sachet is preferably fixed to the receptacle, but most preferably only in the vicinity of the pulling means, i.e. the tabs 45, 46 by means of fixation (51)(52). The fixation could be provided by means of welding, gluing or taping, or a combination of these, but other fixation means could be used as well. Between the fixation points the fluid supply chamber 23 of the receptacle is provided with a surplus of material, resulting in bellow-like folded area 24. This folded area makes an easy elongation of the fluid supply chamber possible. The folded area is further preferably wider than the rest of the fluid supply chamber 23.

Figure 3:
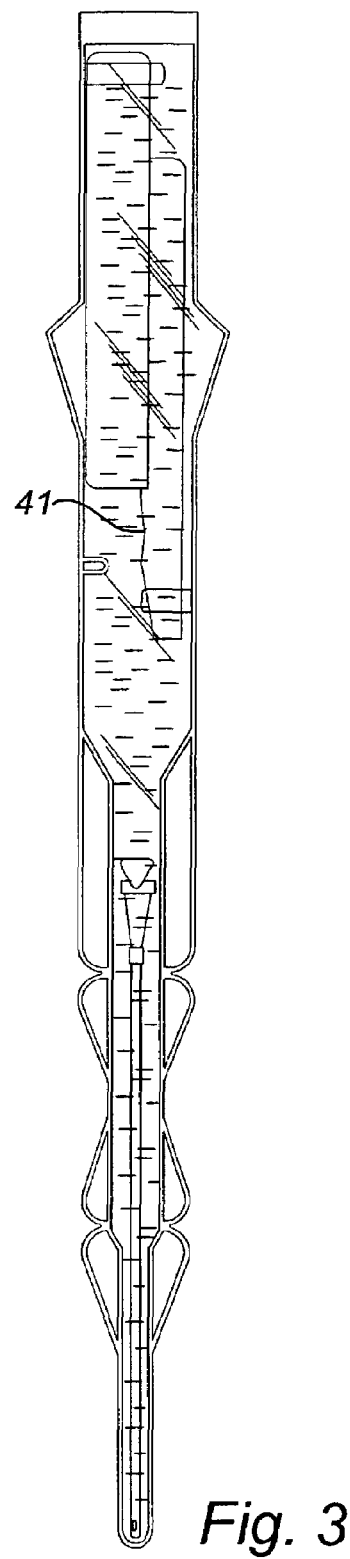
FIG. 3 shows the wetting apparatus shown in FIG. 1 where the wetting fluid sachet is in the opened position.
Figure 4:
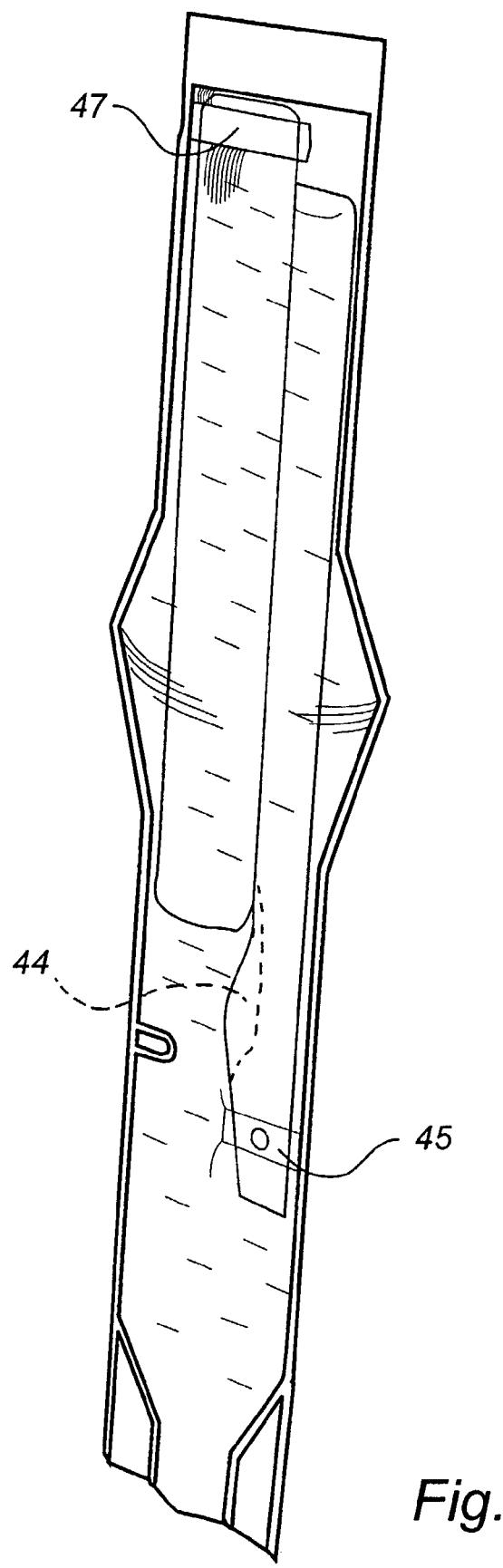
FIG. 4 shows the part of the wetting apparatus shown in FIG. 3 comprising the unopened sachet more in detail.

In FIGS. 3 and 4 the sachet 4 is shown in its opened position, where the contents of the sachet is released into the receptacle 2 to wet the hydrophilic outer coating of the catheter 3.

In the method of wetting the catheter, the user applies a pulling force to the wetting receptacle in such a way that the pulling force is transferred to the wetting container to open the same without rupturing the sealed condition of the wetting receptacle. Preferably, the pulling force is applied in such a way that the pulling means are pulled apart in a separation direction. This could e.g. be made in the following way, with the wetting apparatus described above. The user grips the first tab 45 through the flexible transparent plastics material of the bag 2 and then pulls rearwardly on the pulling portion 47 of the second tab 46, likewise through the flexible transparent plastics material of the bag 2, to cause the tear line 44 to be torn and the wetting fluid to be released into the pocket 21 to wet the catheter 3. Preferably, the sachet 4 contains a sufficient amount of wetting fluid for the pocket 21 to be filled to a level, which results in the insertable length of the catheter 3 being wetted. By insertable length" is meant at least that length of the elongate shaft 32 which is coated with a hydrophilic material, for example PVP, and inserted into the urethra of the patient. Typically, this will be 80–140 mm for a female patient and 200–350 mm for a male patient.

After release of the wetting fluid into the pocket 21 the receptacle is opened, preferably at a tearing section 27, where after the catheter is removed from the bag 21 and used for catherisation. The receptacle and sachet are then disposed of. To facilitate the removal of the catheter from the receptacle and the insertion into the urethra of the patient, at least one area of weakness 27, 28, such as a tear line, is preferably arranged on the receptacle in the area of fluid receiving pocket 21, in which the catheter is placed. Most preferably, two such areas of weakness 27, 28 are provided, and separated in the lengthwise direction of the receptacle. The intermediate part of the receptacle may be used as an insertion aid for guiding and holding the wetted catheter when it is inserted into the urethra. There is therefore no need to directly handle the catheter 3 for insertion thereof into the urethra, which is to advantage as the outer surface of the catheter 3 will be slippery due to the wetting procedure and therefore difficult to grip and furthermore because the possibility of contamination of the catheter 3 at this stage is avoided, whereby the cleanness and sterility of the catheter may be maintained.

The bag or receptacle 2 according to the invention is a closed bag with the sachet 4 and catheter 3 pre-packaged within the bag 2.

The catheter 3 could be sterilised using ethylene oxide. Since the sachet 4 contains sterile water or saline there is no need for sterilising the contents of the sachet 4. Accordingly, the material of the sachet 6 is preferably impermeable to ethylene oxide and water. Non-limiting examples of materials meeting these requirements are poly(vinylidene chloride) (PVDC), aluminium foil laminates or a laminate comprising a metallised film, for example metallised poly(ethylene terepthalate), or a silicon coated film. Other sterilisation processes could of course be used instead, for example by irradiation in which case the fluid in the sachet 4 could be sterilised in situ at the same time as the rest of the components of the apparatus 1. Steam treatment may also be used for sterilisation.

Other types and locations of sachets 4 inside the bag is possible as long as the sachet 4 releases its contents into the pocket 21. For example it is possible to arrange the tear line 44 in an oblique angel relative to the pulling direction. In this case the tearing line will extend essentially in the middle between the two pulling tabs.

Alternatively, it is possible to arrange the pulling tabs laterally on the sachet 4, and thus provide the pulling direction essentially perpendicular to the tearing line. In this case, however, the folding of the fluid supply chamber 23 has to be rearranged in another direction as well.

The expandability of the fluid supply chamber could also be achieved in other ways, such as by the use of a stretchable material. In such a case it is possible to fix the wetting fluid container to the receptacle along its entire surface, and still enable opening of the fluid container without destroying or causing ruptures to the receptacle. However, by providing an area of the fluid container surface which is not fixed to the receptacle, a less degree of stretchability is required.

Even though the receptacle according to the invention is sealed, it is however preferred that the receptacle 2 is provided with an outlet 25, at least when ethylene oxide is the sterilising agent, as this provides a pathway for the ethylene oxide to enter and exit the inside of the receptacle.

Figure 5:
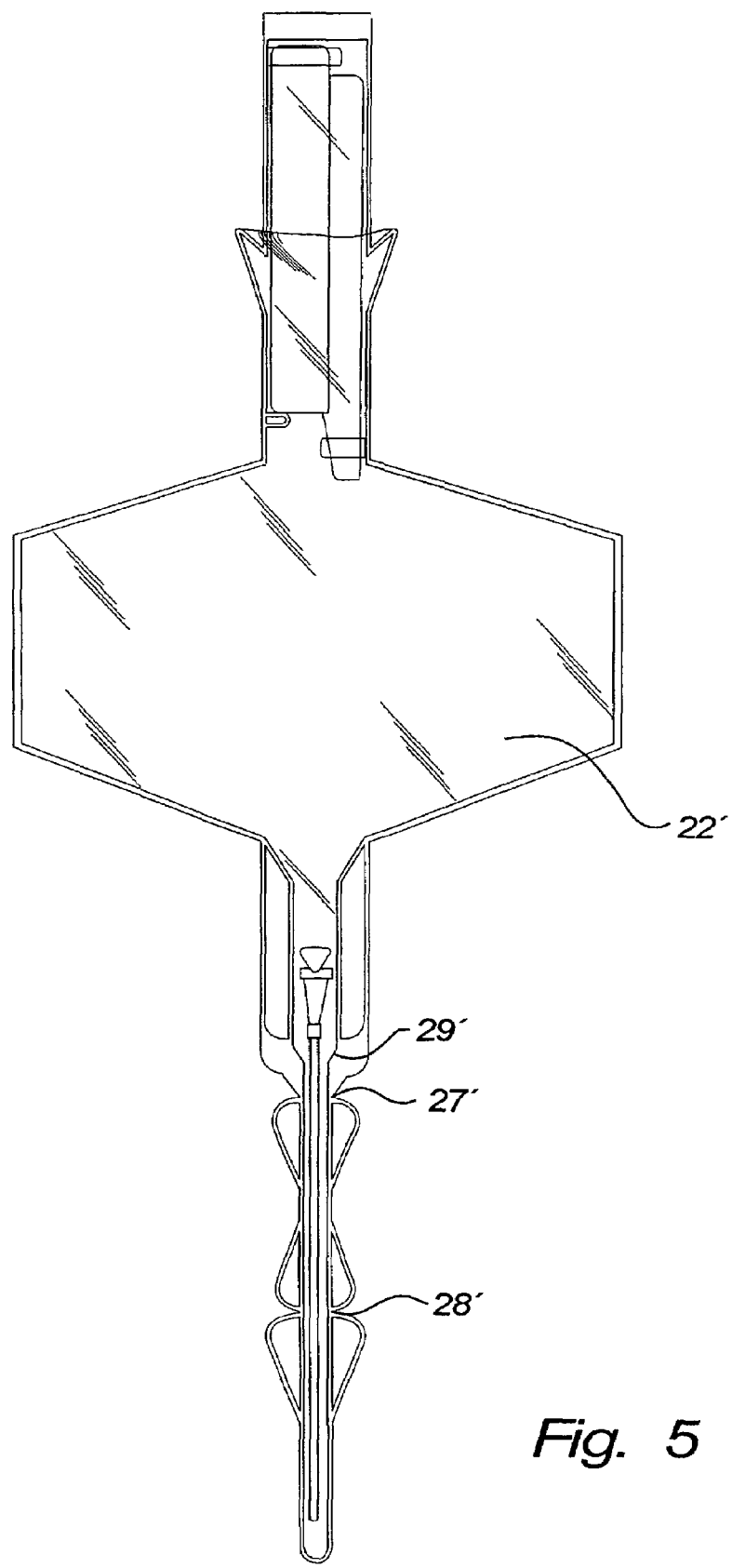
FIG. 5 shows a wetting apparatus according to another embodiment of the invention.

In still another embodiment, shown in FIG. 5, the intermittent chamber 22' of the receptacle 2 may be used as a urine bag. In this case, after wetting of the catheter 3 for the predetermined duration in the same manner as described above, the bag 2 is turned upside down and the forwardmost portion of the pocket 21 torn off. The elongate shaft 32 of the catheter 3 is then maneuvered through the opening in the forward end of the pocket 21 and pulled out until the flared rearward portion 31 forms a mechanical seal connection with the opening at a restriction 29' of the receptacle. Thereafter the catheter is inserted into the urethra of the patient. Two separated areas of weakness 27', 28' may be used as an insertion aid even in this embodiment. However, in this case the areas of weakness should be placed beneath the restriction 29'. Except the above mentioned differences, the same as discussed above regarding the first embodiments applies to this alternative embodiment as well.

In the exemplary embodiments hereinabove described with reference to drawings the supply of wetting fluid for wetting of the hydrophilic urinary catheter takes the form of a separate sachet integrated into the wetting receptacle, and being easily dischargeable without breaking or rupturing the receptacle. It will be appreciated by those versed in the art that several alternatives similar to those described above could be used without departing from the spirit of the invention, such as other types of fluid containers, different ways to provide the expandability of the receptacle etc.

The invention claimed is:

1. A wetting apparatus for wetting a hydrophilic urinary catheter, comprising:
    a wetting fluid container containing a wetting fluid and being openable by the application of a pulling force thereto:
    a wetting receptacle; and
    a hydrophilic urinary catheter to be wetted by said wetting fluid and being arranged within said wetting receptacle,
    wherein the wetting fluid container is arranged within the wetting receptacle, and the wetting receptacle is extendable, for opening the wetting container without rupturing a sealed condition of the wetting receptacle, and
    wherein the wetting fluid container is provided with at least two pulling means for applying said pulling force for opening the container and is fixed to the wetting receptacle only in the vicinity of the pulling means.

2. The wetting apparatus according to claim 1, wherein the wetting fluid container is openable by pulling said pulling means apart in a separation direction, said wetting receptacle being extendable at least in said separation direction.

3. The wetting apparatus according to claim 2, wherein at least one of the pulling means is a tab which on application of a predetermined pulling force thereto causes the wetting fluid container to open.

4. The wetting apparatus according to claim 1, wherein the wetting fluid container is fixed to the wetting receptacle by welding.

5. The wetting apparatus according to claim 1, wherein the wetting receptacle is at least partly formed of a stretchable material, enabling the extendibility of the receptacle.

6. The wetting apparatus according to claim 1, wherein the wetting fluid container takes the form of a sachet.

7. The wetting apparatus according to claim 1, wherein the wetting fluid is sterile water or a saline solution.

8. The wetting apparatus according to claim 7, wherein the wetting fluid container is impermeable to ethylene oxide and water or saline solution.

9. The wetting apparatus according to claim 1, wherein the wetting fluid container is made of aluminum foil laminate, poly(vinylidene chloride) or a laminate comprising a metallized film, or a silicon oxide coated film.

10. The wetting apparatus according to claim 1, wherein the wetting receptacle is a urine collection bag.

11. A wetting apparatus for wetting a hydrophilic urinary catheter, comprising:
a wetting fluid container containing a wetting fluid and being openable by the application of a pulling force thereto;
a wetting receptacle; and
a hydrophilic urinary catheter to be wetted by said wetting fluid and being arranged within said wetting receptacle,
wherein the wetting fluid container is arranged within the wetting receptacle, and the wetting receptacle is extendable, for opening the wetting container without rupturing a sealed condition of the wetting receptacle, and
wherein the wetting receptacle comprises at least one folded section to make the receptacle extendable.

12. The wetting apparatus according to claim 11, wherein the wetting fluid container is provided with at least two pulling means for applying said force for opening the container and said surface layer of the wetting receptacle has a dimension between the pulling means exceeding the distance between the pulling means, when the wetting fluid container is not opened.

13. The wetting apparatus according to claim 11, wherein the wetting receptacle has a restricted dimension perpendicular to the pulling direction in which said folded section is unfolded, such that said unfolding is not restricted by the wetting fluid container.

14. The wetting apparatus according to claim 13, wherein the wetting receptacle, at said folded section has an inner, cross-sectional dimension perpendicular to the extension direction of the receptacle significantly exceeding the corresponding outer, cross-sectional dimension of the wetting fluid container.

15. The wetting apparatus according to claim 11, wherein the at least one folded section is a bellow like folding to make the receptacle extendable.

16. The wetting apparatus according to claim 11, wherein the wetting fluid container is provided with at least two pulling means for applying said pulling force for opening the container.

17. The wetting apparatus according to claim 11, wherein the wetting fluid container is openable by pulling said pulling means apart in a separation direction, said wetting receptacle being extendable at least in said separation direction.

18. The wetting apparatus according to claim 17, wherein at least one of the pulling means is a tab which on application of a predetermined pulling force thereto causes the wetting fluid container to open.

19. The wetting apparatus according to claim 11, wherein the wetting fluid container is fixed to the wetting receptacle by welding.

20. The wetting apparatus according to claim 11, wherein the wetting receptacle is at least partly formed of a stretchable material, enabling the extendibility of the receptacle.

21. A wetting apparatus for wetting a hydrophilic urinary catheter, comprising:
a wetting fluid container containing a wetting fluid and being openable by the application of a pulling force thereto;
a wetting receptacle; and
a hydrophilic urinary catheter to be wetted by said wetting fluid and being arranged within said wetting receptacle,
wherein the wetting fluid container is arranged within the wetting receptacle, and the wetting receptacle is extendable, for opening the wetting container without rupturing a sealed condition of the wetting receptacle, and
wherein the wetting fluid container comprises an area of weakness which is opened on the application of the pulling force, the area of weakness extending at an oblique angle to a direction towards the catheter in the wetting receptacle.

22. The wetting apparatus according to claim 21, wherein the area of weakness in the wetting fluid container is arranged in a part of the container facing the catheter in the wetting receptacle.

23. The wetting apparatus according to claim 22, wherein at least one of the pulling means is a tab which on application of a predetermined pulling force thereto causes the wetting fluid container to open and the wetting fluid container presents a forward edge facing the catheter in the wetting receptacle; the area of weakness extends rearwardly from the forward edge; the wetting container comprises two tabs of which a first tab extends rearwardly from the forward edge on a first side of the area of weakness and is of such dimensions that it rearwardly projects beyond the wetting fluid container, and of which a second tab extends forwardly from the forward edge on a second, opposite side of the area of weakness; wherein the application of a rearward pulling force on the first tab relative to the second tab causes the area of weakness to tear and the wetting fluid container to be opened.

24. The wetting apparatus according to claim 22, wherein at least one of the pulling means is a tab which on application of a predetermined pulling force thereto causes the wetting fluid container to open and the wetting fluid container presents a forward edge facing the catheter in the wetting receptacle; the area of weakness extends rearwardly from the forward edge; the container comprises two tabs, of which a first tab extends laterally relative to the forward edge on a first side relative to the area of weakness, and of which a second tab extends laterally from the forward edge on a second, opposite side of the area of weakness relative to the first tab; wherein the application of a predetermined lateral pulling force on the first tab relative to the second tab causes the area of weakness to tear and the wetting fluid container to be opened.

25. The wetting apparatus according to claim 21, wherein at least one of the pulling means is a tab which on application of a predetermined pulling force thereto causes the wetting fluid container to open and the wetting fluid container presents a forward edge facing the catheter in the wetting receptacle and a rearward edge facing away from the catheter in the wetting receptacle, whereby the area of weakness extends between the forward and rearward edge; the container comprises two tabs, of which a first tab extends forwardly on the forward edge on the side closest to the area of weakness, and of which a second tab extends rearwardly from the rearward edge on the side closest to the area of weakness; and application of a predetermined rearward pulling force on the first tab relative to the second tab causes the area of weakness to tear and the wetting fluid container to be opened.

26. The wetting apparatus according to claim 21, wherein the wetting fluid container is provided with at least two pulling means for applying said pulling force for opening the container.

27. The wetting apparatus according to claim 21, wherein the wetting fluid container is openable by pulling said pulling means apart in a separation direction, said wetting receptacle being extendable at least in said separation direction.

28. The wetting apparatus according to claim 26, wherein at least one of the pulling means is a tab which on application of a predetermined pulling force thereto causes the wetting fluid container to open.

29. The wetting apparatus according to claim 21, wherein the wetting fluid container is fixed to the wetting receptacle by welding.

30. The wetting apparatus according to claim 21, wherein the wetting receptacle is at least partly formed of a stretchable material, enabling the extendibility of the receptacle.

* * * * *